United States Patent [19]

Woods et al.

[11] Patent Number: 4,583,534
[45] Date of Patent: Apr. 22, 1986

[54] COLLAPSIBLE CHAIN MAIL STRUCTURE

[76] Inventors: John T. Woods; Margaret H. Woods, both of 811 Loma Vista Pl., Santa Paula, Calif. 93060

[21] Appl. No.: 738,243

[22] Filed: May 28, 1985

[51] Int. Cl.[4] .......................... A61F 3/00; A61F 5/04; A41C 1/00

[52] U.S. Cl. ................ 128/80 R; 128/87 R; 128/531; 87/9; 383/117

[58] Field of Search .............. 128/80 R, 89 A, 87 A, 128/87, 80, 1 R, 75, 535, 531, 77; 383/117; 87/11, 9, 8, 2; 40/300; 254/134.3 FT; 428/36

[56] References Cited

U.S. PATENT DOCUMENTS

| | | | |
|---|---|---|---|
| 368,241 | 8/1887 | Roberts | 128/531 |
| 423,490 | 3/1890 | Roberts | 128/531 |
| 1,833,163 | 11/1931 | Ischinger | 128/535 |
| 2,166,748 | 7/1939 | Bloch | 87/2 |
| 2,936,257 | 5/1960 | Nailler et al. | 87/9 |
| 3,122,806 | 3/1964 | Lewis | 87/6 |
| 3,307,546 | 3/1967 | Cherio et al. | 87/2 |
| 3,483,907 | 12/1969 | Corridon | 383/117 |
| 3,768,643 | 10/1973 | Bruno | 383/117 |
| 3,916,550 | 11/1975 | Dzus | 40/300 |
| 3,976,062 | 8/1976 | Cox | 128/87 R |
| 4,029,090 | 6/1977 | Dawson, Jr. | 128/87 R |
| 4,070,027 | 1/1978 | Kifferstein et al. | 128/87 R |
| 4,098,405 | 7/1978 | Botvin | 383/117 |
| 4,144,881 | 3/1979 | Chappell | 128/80 R |
| 4,228,207 | 10/1980 | Porte et al. | 87/7 |
| 4,247,005 | 1/1981 | Buxton | 383/117 |
| 4,271,329 | 6/1981 | Perelmuter | 87/9 |
| 4,401,107 | 8/1983 | Haber et al. | 128/1 R |
| 4,532,163 | 7/1985 | Hoppie | 428/36 |

FOREIGN PATENT DOCUMENTS

| | | | |
|---|---|---|---|
| 504591 | 12/1954 | Italy | 87/9 |
| 8303752 | 11/1983 | PCT Int'l Appl. | 128/1 R |
| 37687 | 3/1914 | Sweden | 87/9 |
| 74283 | 2/1917 | Switzerland | 128/87 R |
| 131707 | 5/1929 | Switzerland | 383/117 |
| 591185 | 2/1978 | U.S.S.R. | 128/75 |

*Primary Examiner*—Robert Peshock
*Assistant Examiner*—J. R. Hakomaki
*Attorney, Agent, or Firm*—Albert O. Cota

[57] ABSTRACT

A structure utilizing a plurality of hollow X-sections connected together by a rope threaded through each leg. A first ring body and a second ring body are located above and below the assembled X-sections and contain a series of spaced holes through which the ropes extend. Tightening means in multiple form, or single form, allow the ropes to be retracted through the holes, tensioning the entire assembly until all of the interface joints are tight. This provides a rigid structured cylinder through which a body member, such as an arm, leg, back or neck may be inserted to act as a splint or assist the normal body movements when walking.

7 Claims, 17 Drawing Figures

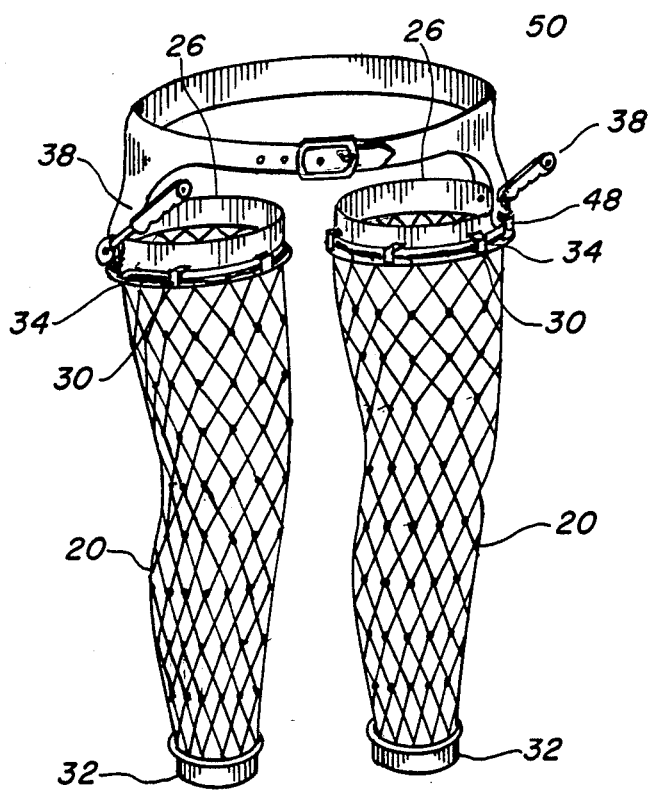
FIG. 1
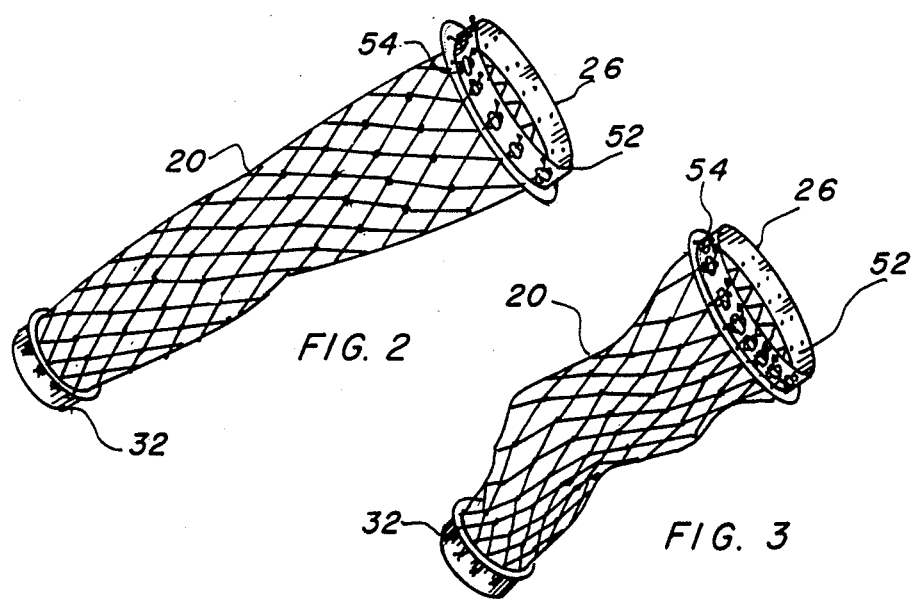
FIG. 2
FIG. 3

COLLAPSIBLE CHAIN MAIL STRUCTURE

TECHNICAL FIELD

This invention relates to ambulatory body member braces in general, and more specifically to a collapsible structure loosing basic shape when loosened and becoming rigid and of a predetermined or infinitely different configuration when tensioned.

BACKGROUND ART

Previously, many types of braces have been used in endeavoring to provide an effective means to strengthen and stiffen a body member, such as a leg. In most cases this brace adds structure that is hinged and pivoted in the same places as required by human movement. Other prior art teaches an elastic or pneumatic support to inhibit movement. A search of the prior art did not disclose any patents that directly read on the claims of the instant invention. However, the following U.S. patents were considered related:

| U.S. Pat. No. | Inventor | Issue Date |
|---|---|---|
| 4,370,978 | Palumbo | Feb. 1, 1983 |
| 4,366,813 | Nelson | Jan. 4, 1983 |
| 4,144,881 | Chappell | Mar. 20, 1979 |
| 4,089,064 | Chandler, Jr. | May 16, 1978 |
| 3,923,045 | Talati et al | Dec. 2, 1975 |
| 3,799,159 | Scott | Mar. 26, 1974 |
| 3,203,285 | Schmidt | Aug. 31, 1965 |
| 2,632,440 | Hauser et al | Mar. 24, 1953 |
| 2,111,018 | Ahler | Mar. 15, 1938 |
| 2,107,095 | Wagner | Feb. 1, 1938 |

Palumbo teaches a pad knee brace having separate resilient pads located to support specific areas related to extensor mechanism problems.

Nelson discloses a similar device as above, except resilient elongated stays are located in pockets to provide lateral support.

Chappell utilizes a prosthetic device formed of interlocking crescent shaped discs locked in a chain manner with tongue and grooved relationship limiting the movement to a single plane.

Chandler, Jr. employs a light elastomeric fabric material in conjunction with a second set of fabrics attached to stockings with an overlying knee grip providing support in the knee area with a tension load in the fiber connecting material to the wearers waist.

Talati et al practices an ambulation device for hemiplegics having a torso-encircling band and shaft for rotation about the longitudinal axis.

Scott applies a hydraulic knee flexion device, which is flexible when unlocked, however, contains a hydraulic system holding a cable immovable permitting a spring to bend when flexion is desired.

Schmidt teaches a wrench utilizing a plurality of handle segments adapted to be interlocked and engaged with each other utilizing a flexible cable that is secured to the wrench head and extends through the handle segments. The segments are configured to have one side longer than the other and are interlocking allowing a variety of rotational orientations depending upon the rotational position of each individual handle segment relative to each other. The cable is tensioned by a threaded extensible member screwed into a bushing, shortening the cable in relation to the length of the total segments, thereby causing a rigid handle to be formed.

Hauser et al practices a leg and joint lock permitting crippled individuals to walk. The damaged leg is enclosed from the thigh to the ankle with a double acting joint following the normal bending action at the knee.

Ahler employs a belt to be worn around the waist with a pivoted spring loaded structural upper section with a support plate connecting to a leg brace above the pivot point for vertically swinging the leg brace in a forward striding motion.

Finally, Wagner takes advantage of a brace with a lower and upper section having a foot saddle pivotally mounted on the lower section. A knee joint connects the two together and contains single discs on one end journalled thereon.

DISCLOSURE OF THE INVENTION

Many attempts have been made to provide an orthopedic prosthetic device which allows full and complete motion of a leg, or other member of the body, and yet become rigid enough to support weight when stiffened. It is, therefore, a primary object of the invention to allow a tubular structure to be completely flexible enough so as to be fitted upon a leg easily and conform in shape thereunto while in its collapsed, pliable state, and when actuated, become rigid as a solid tube. The invention performs this object by tightening a plurality of flexible wires or wire ropes that are threaded upon a series of mated hollow X-shaped sections. Inasmuch as the rope connects each member in two planes while no tension is applied, the assembly conforms to any shape within its separated bounds. When tension is applied to the rope each section is brought into contact with mating ends of the next section creating a fixed condition at each joint making the entire assembly rigid within each sections structural limitations.

The capability of a variable diameter tube is also an important object and is accomplished by changing the size of the X-sections at the appropriate location, either increasing or decreasing the length of the connecting members. This variable size allows the contour of the leg to be duplicated providing an even distribution of pressure upon the supported leg. In one embodiment the invention may be worn in conjunction with a waist band holding one or two cylindrical shaped assemblies to be fitted upon the users legs. This allows a walking brace to support the leg when required and be flexible when necessary, simulating the walking function. Another embodiment may be used as a splint for a broken or injured leg, arm, back or neck. This embodiment is collapsed for transportation and storage and becomes rigid when the rope is tensioned about the persons limb.

Another object of the invention provides a quick and easy to operate tensioning and release mechanism. Again, two embodiments are taught, the preferred embodiment utilizes an eccentric rotatable device attaching all of the ropes together. A handle rotates a spool tensioning all of the ropes simultaneously and is fastened by locking the handle into place into a guide. The second embodiment utilizes individual ropes that are tensioned separately by the use of a spring loaded plunger having a slot lined up with a pair of holes in an attachable body and the rope directed therethrough. Each rope is tensioned by pulling on the upper end while depressing the plunger until it is taut. The rope then retained by the spring tension of the plunger in shear fashion against the hole and slot. In both cases the tension is easily obtained by simple manual manipulation and release is achieved by the reverse procedure.

Still another object of the invention is the structure by itself which is open, light in weight, and easy to clean. Since individual members make up the body and each is only slightly larger than the rope threaded therethrough, only a small portion of the surface is covered with structure, leaving the balance open exposing the users body member. Each individual X-shaped member is hollow and small in diameter, very little weight is taken by the largest portion of the invention.

Yet another object of the invention is the ease of maintenance afforded by the multiple members that may be replaced if broken or damaged. Individual X-shaped members are attached together with only a rope, which may be removed and replaced with separate members replaced with equal ease.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is a partial isometric view of the embodiment having multiple tightening means, including a waist band allowing the user to simulate walking movements.

FIG. 2 is a partial isometric view of the single tightening means embodiment shown in its tensioned position with each rope taut.

FIG. 3 is a partial isometric view of the same embodiment as above with the rope loose in its collapsed condition.

BEST MODE FOR CARRYING OUT THE INVENTION

The best mode for carrying out the invention is presented in the terms of a preferred and second embodiment. Both embodiments use the same X-sections and basically the same rings, except the preferred embodiment is tightened all at the same time and the second embodiment is individually tensioned.

Figure 4:
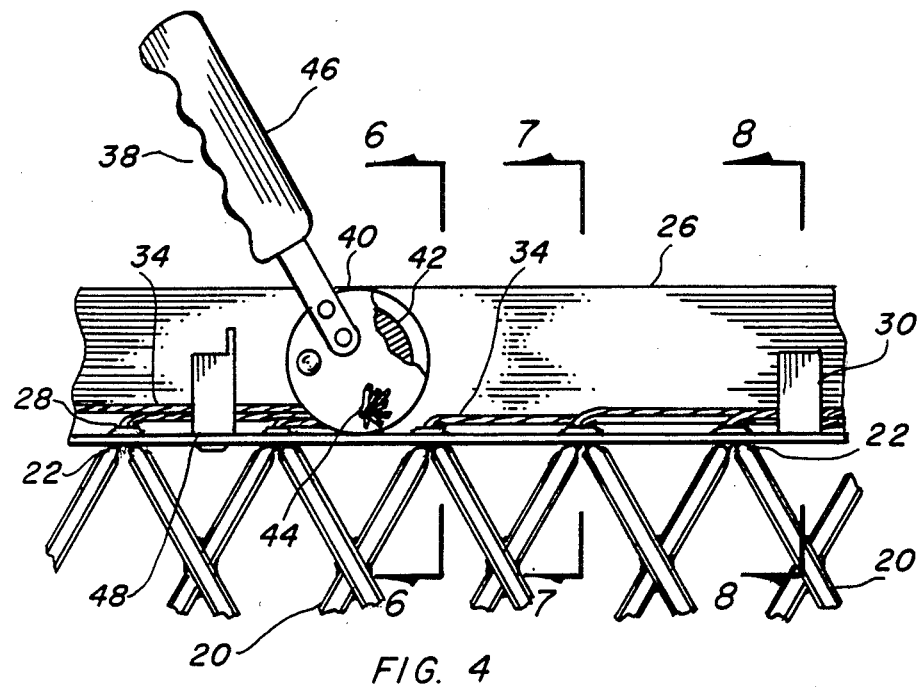
FIG. 4 is an elevation view of the upper portion of the preferred embodiment.
Figure 5:
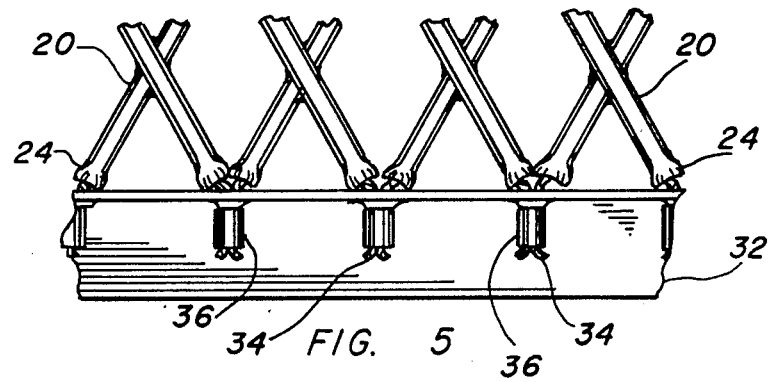
FIG. 5 is an elevation view of the lower portion of the preferred embodiment.
Figures 6, 7, 8:
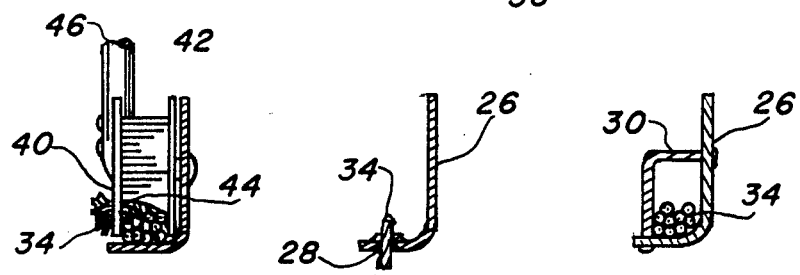
FIG. 6 is a cross-sectional view taken along lines 6—6 of FIG. 4.
FIG. 7 is a cross-sectional view taken along lines 7—7 of FIG. 4.
FIG. 8 is a cross-sectional view taken along lines 8—8 of FIG. 4.
Figure 9:
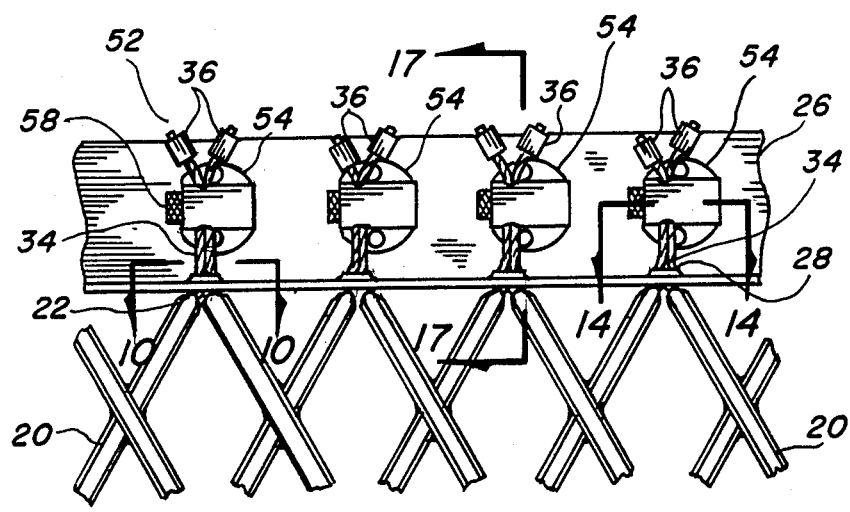
FIG. 9 is an elevation view of the upper portion of the second embodiment.
Figure 10:
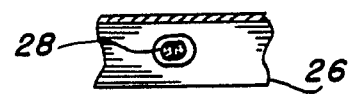
FIG. 10 is a cross-sectional view taken along lines 10—10 of FIG. 9.
Figures 11, 12, 13:
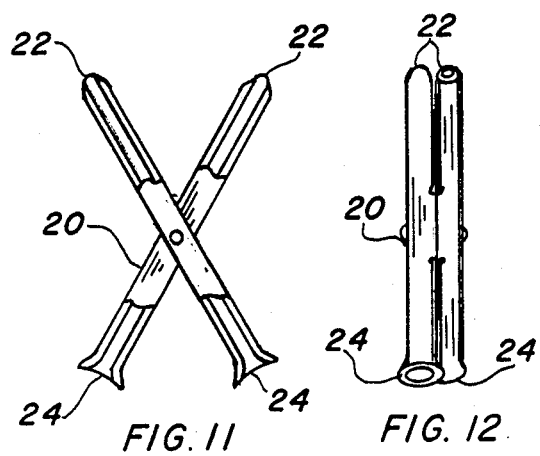
FIG. 11 is a front elevation view of an X-section completely removed from the invention for clarity.
FIG. 12 is a side view of an X-section completely removed from the invention for clarity.
FIG. 13 is a front elevation view of another X-section cut away for clarity.
Figure 14:
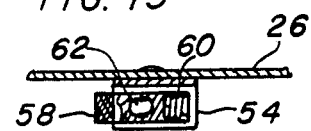
FIG. 14 is a cross-sectional view taken along lines 14—14 of FIG. 9.
Figures 15, 16:
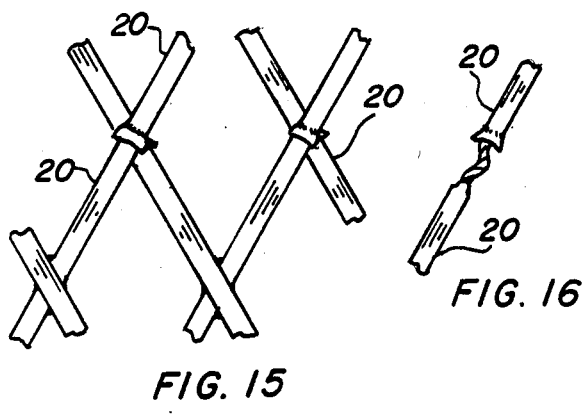
FIG. 15 is a partial view of the X-sections tensioned together tightly.
FIG. 16 is a partial view of two of the X-sections connected loosely.
Figure 17:
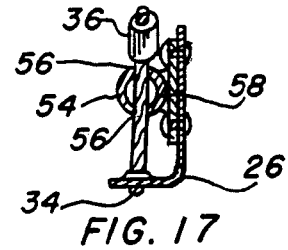
FIG. 17 is a cross-sectional view taken along lines 17—17 of FIG. 9.

The preferred embodiment is depicted in FIGS. 1 and 4–8 and consists of a plurality of articulated hollow X-sections 20 nested together, or contiguous with each other at the extremities. Two of the four ends have a male radiused projection 22, while the other two contain a female socket 24. This allows the ends 22 and 24 to mate together forming a type of structural joint. The socket 24, however, may be slightly larger allowing some movement in the joint when nested together allowing a specific shape to be maintained by the number and size of assembled X-sections. Each X-section 20 is hollow with a cross-over or cavity in the center allowing a clear passageway through each set of legs from opposed ends. The sections 20 may be fabricated of any material suitable for the purpose, such as metal, or the like, with a thermoplastic or thermosetting plastic being preferred. A suitable plastic substance would be a composition such as polypropylene, styrene, polyethylene, cellulose acetate, nylon, or the like, injection molded into the desired form. The X-section may vary in size and may cross over and be hinged with a pin as shown in FIGS. 11 and 12 or may be planar as in FIG. 13. A rigid or semi-rigid composition allows the strength to be maintained by the assembly with sufficient resiliency to accommodate the intended purpose.

A first ring body 26, normally utilized on the top, contains an outwardly extending flange having a plurality of holes. The ring, therefore, has a continuous loop of material the same direction as the assembly, and a right angle flange at one end, preferably the bottom. These holes 28 are pierced or formed into the parent material and have a radical portion on the bottom formed upward into an oval shaped hole 28 sized to accommodate two round elements. These holes 28 are equally spaced and stagger one with the other in an equal distance away from the periphery of the flange. On the preferred embodiment a plurality of keepers 30 in angle shape, are positioned in spaced relationship between the end of the flange and the band acting as a guide and retainer for elements placed therein. These keepers 30 may be attached with any common method known in the art. The material of both the ring 26 and the keeper 30 is thermoplastic, as previously described, or a metal such as magnesius, steel, or aluminum.

A second ring body 32 is similar in form and material as the first body 26, except the flange is reversed and no keepers are present. This ring 32 is positioned on the lower or ankle portion of the wearers body, and as such, is of sufficient diameter to place ones foot through. The holes 28 are of the same form, except reversed with the largest radial section on the bottom.

A plurality of interconnecting stranded ropes 34 are threaded through the holes 28 in the second ring body 32, the hollow inside portion of the X-sections 20, and the holes 28 in the first ring body 26. These ropes are flexible and have sufficient length to allow the assembly to flex at each joint and interface. The rope 34 may be of a natural fiber, plastic fiber as polyester, nylon, or the like, or may be a wire rope of metal covered with a plastic sleeve. The types of metal may be galvanized steel, copper, aluminum, or stainless steel, as preferred by the application as all of the above materials and others will function properly in the invention. A retainer 36 is fastened at each end of the rope 34 after it is threaded into place to contain the assembled parts together. When the rings 26 and 32 are assembled with the X-sections 20 and the ropes 34 are threaded and retained the assembly forms an interconnected collapsible structure that may be positioned easily upon a member of ones body, such as an arm, or leg, and as such, is free to move in any direction during the process.

The assembly is made rigid by tightening means that apply tension to the X-sections 20 pulling them together with the rope 34. The preferred tightening means is best depicted in FIGS. 1, 4–8, and is designated as multiple tightening means 38 and tensions all of the ropes 34 simultaneously. This is accomplished by the use of an eccentric spool 40 that is rotatably attached to the first ring 26. An axial groove 42 is located on the periphery of the spool 40 with a bore 44 on the exposed sides. A handle 46 extends from the spool upward from the ring 26 with a guide 48 positioned on the ring 26 near the spool 40. This guide 48 has an aperture to hold the ropes 34 and receive and retain the handle 46 when in the tensioned position. The ropes 34 are positioned from the holes 28 in the bodies 26 and 32, through the X-sections 20 and are guided around the first body 28 near the flange, and are held in place with the keepers 30. When the handle 46 is rotated the ropes are pulled around the first body ring 26 until they are taut and then the handle may be locked into place in the guide 48.

A waist band 50 connects to one or more first ring body(s) 26 providing an assembly that may be worn or ones person allowing alternate tightening and loosening of the tightening means 38 in such a manner as to simulate walking movements.

The second embodiment is pictorially illustrated in FIGS. 2, 3, and 9–17, and contains the same X-sections 20 with the first ring 26 and the second ring 32 complete with ropes 34. The difference lies in the method of tensioning the ropes 34. This embodiment utilizes single tightening means 52 allowing individual tension of each rope independent of the others. This is achieved by the use of an attachable body 54 with a centrally located cavity on the inside. A pair of oval shaped openings 56 at right angles to the attaching ring 26. These openings 56 are slightly larger than the stranded rope 34 allowing a slide fit. A plunger 58 that is smaller in diameter than the cavity in the body 54 is slideably located within the body and is in front of a compression spring 60. The plunger 58 also has a slot 62 the same approximate size as the oval opening 56 in the body 54, this allows a pair of ropes 34 to be threaded through the openings 56 and 62 when the plunger 58 is manually depressed thereby aligning the openings. As the plunger 58 is released the spring 60 urges the plunger 58 against the ropes 34 in shear fashion between the openings 56 and 62 holding the ropes tightly within these confines. To tension the ropes 34 the operator grasps the retainers 36 at the end of the rope 34 with one hand and with the other depresses the plunger 58 loosening the contact allowing the ropes 34 to be pulled upwardly creating the desired amount of tension. When the plunger 58 is released, the ropes 34 maintain their status through the compressive force.

This second embodiment is best suited for attachment to the body in the form of a temporary splint for the arm or leg where the pressure may be individually maintained and rigidity of the body member is easily and completely accomplished. Other utility may also be utilized by the invention, not necessarily of a medical nature, but any structure requiring rigidity in one mode and flexibility in the other.

While the invention has been described in complete detail and pictorially shown in the accompanying drawings, it is not to be limited to such details, since many changes and modifications may be in the invention without departing from the spirit and the scope thereof. Hence, it is described to cover any and all modifications and forms which may come within the language and scope of the appended claims.

We claim:

1. A collapsible chain mail structure comprising:
   (a) a plurality of articulated hollow X-sections of varying size, positioned with each end contiguous with another forming a circular sleeve;
   (b) a first ring body having an outwardly extending flange containing a plurality of holes spaced co-equal to the ends of said X-sections mating thereupon;
   (c) a second ring body having an outwardly extending flange containing a plurality of holes spaced co-equal to the ends of said X-sections mating thereupon;
   (d) a plurality of interconnecting stranded ropes threaded through each extremity of said X-section crossing in the center and penetrating the appropriate holes in said first ring body on one end and matching holes in said second ring body on the other end forming an interconnected collapsible structure; and,
   (e) multiple tightening means tensioning said plurality of stranded ropes on said first ring body in such a manner as to tension all of the ropes simultaneously tying the X-sections together structurally forming a rigid enclosure between said first and second ring for containing a body member therewithin.

2. The apparatus as recited in claim 1 wherein said X-section further comprises: a male projection on the first two ends and;
   a female socket on the second two ends opposite each other allowing the first ends to embracingly mate with the second ends forming a structural joint therebetween.

3. The apparatus as recited in claim 1 wherein said multiple tightening means further comprises:
   (a) an eccentric spool means rotatably attached to said first ring body having an axial groove therearound and rope joining means;
   (b) a handle distending from said spool for manual manipulation thereof; and,
   (c) a guide distal proximate to said spool having a rope aperture therethrough and handle attachment means to receive and hold said handle in place when mated thereupon, tightening all of said ropes simultaneously when said ropes are positioned from said holes in said first ring body through the aperture into said spool rope joining means when the spool is manually rotated with the handle until all of the ropes are taut and the handle is locked into place with the handle attaching means.

4. The apparatus as recited in claim 1 further comprising: a waist band having means to connect said first ring body thereupon providing an assembly that may be worn on ones person allowing alternate tightening and loosening of said multiple tightening means in such a manner as to allow a person to manually simulate walking movements.

5. A collapsible chain mail structure comprising:
   (a) a plurality of articulated hollow X-sections of varying size positioned with each end contiguous with another forming a circular sleeve.

(b) a first ring body having an outwardly extending flange with a plurality of holes spaced co-equal to the ends of said X-sections for mating thereupon;

(c) a second ring body having an outwardly extending flange containing a plurality of holes spaced co-equal to the ends of said X-sections mating thereupon;

(d) a plurality of interconnecting stranded ropes threaded through each extremity of said X-section, crossing in the center and penetrating the appropriate holes in said first ring body on one end and matching holes in said second ring body on the other end forming an interconnected collapsible structure; and, (e) single tightening means tensioning said stranded ropes on said first ring body in such a manner as to individually tension each rope independent of the others tying the X-sections together structurally forming a rigid enclosure between said first and second ring for containing a body member therewithin.

6. The apparatus as recited in claim 5 wherein said X-section further comprises: a male projection on the first two ends and; a female socket on the second two ends opposite each other allowing the first ends to embracingly mate with the second ends forming a structural joint therebetween.

7. The apparatus as recited in claim 5 wherein said single tightening means further comprises a plurality of individual members each having:

(a) attachable body means having a centrally located cavity therein with through oval shaped openings penetrating said body at right angles slightly larger than said stranded rope for receiving the rope therethrough;

(b) a plunger slightly smaller in diameter than said body means cavity having a slot therethrough for receiving said stranded rope when slideably positioned within said body cavity linearly aligning the slot with the round opening forming a shear compression joint upon said rope; and, (c) a compression spring within said cavity drivingly urging said plunger against said rope when held within said round openings creating a compressive shear force holding the rope in place, and yet allowing release when manually depressing said plunger further into said cavity against the spring pressure for adjustment thereof.

* * * * *